United States Patent
Wang et al.

(10) Patent No.: US 10,093,952 B2
(45) Date of Patent: Oct. 9, 2018

(54) METHOD FOR PREPARING YEAST BETA-D-GLUCAN USING SOLUBILIZATION TECHNOLOGY BASED ON MOLECULAR ASSEMBLY

(71) Applicant: Institute of Agro-Products Processing Science and Technology, CAAS, Beijing (CN)

(72) Inventors: Qiang Wang, Beijing (CN); Hongzhi Liu, Beijing (CN); Li Liu, Beijing (CN); Aimin Shi, Beijing (CN); Hui Hu, Beijing (CN); Yanan Li, Beijing (CN); Weijing Lin, Beijing (CN); Yuquan Duan, Beijing (CN); Jie Gao, Beijing (CN); Xiaoyong Liu, Beijing (CN)

(73) Assignee: Institute of Agro-Products Processing Science and Technology, CAAS, Beijing (CN)

( * ) Notice: Subject to any disclaimer, the term of this patent is extended or adjusted under 35 U.S.C. 154(b) by 82 days.

(21) Appl. No.: 14/845,305

(22) Filed: Sep. 4, 2015

(65) Prior Publication Data
US 2016/0333383 A1 Nov. 17, 2016

(30) Foreign Application Priority Data
May 14, 2015 (CN) .......................... 2015 1 0245370

(51) Int. Cl.
*C12P 19/04* (2006.01)
*C08B 37/00* (2006.01)

(52) U.S. Cl.
CPC .......... *C12P 19/04* (2013.01); *C08B 37/0024* (2013.01)

(58) Field of Classification Search
None
See application file for complete search history.

(56) References Cited

U.S. PATENT DOCUMENTS

2003/0153746 A1* 8/2003 Van Lengerich ....... C08B 30/10
536/123.12

FOREIGN PATENT DOCUMENTS

| CN | 101020915 A | 8/2007 |
|---|---|---|
| CN | 103044572 A | 4/2013 |
| CN | 103059161 A | 4/2013 |

OTHER PUBLICATIONS

Wang et al., English machine translation of CN 103044572(A) published Apr. 17, 2013 (of record).*
Wang et al., English machine translation of CN 103059161(A) published Apr. 24, 2013 (of record).*

* cited by examiner

*Primary Examiner* — Soren Harward
*Assistant Examiner* — Paul D. Pyla
(74) *Attorney, Agent, or Firm* — Edwin S. Flores; Daniel J. Chalker; Chalker Flores, LLP

(57) ABSTRACT

The present invention provides a method for preparing yeast beta-D-glucan using a solubilization technology based on molecular assembly, comprising the following steps: (1) micro-fluidizing an enzymatic hydrolysate of yeast cell walls at 70 to 200 MPa, and then centrifuging to obtain a precipitate; (2) resuspending the precipitate obtained in step (1) with a ionic liquid, then dispersing to obtain a solution; wherein the ionic liquid is 1-ethyl-3-methylimidazolium acetate or 1-allyl-3-methylimidazolium chloride; (3) centrifuging the solution obtained in step (2), and then adding ethanol, centrifuging and collecting a precipitate; (4) resuspending the precipitate obtained in step (3) with water, then centrifuging and collecting a supernatant. Preferably, the method further comprises (5): spray drying the supernatant obtained in step (4) to obtain a yeast beta-D-glucan powder. The yeast beta-D-glucan obtained in the present invention has high purity and good solubility, which advantageously enlarges its application range.

19 Claims, 1 Drawing Sheet

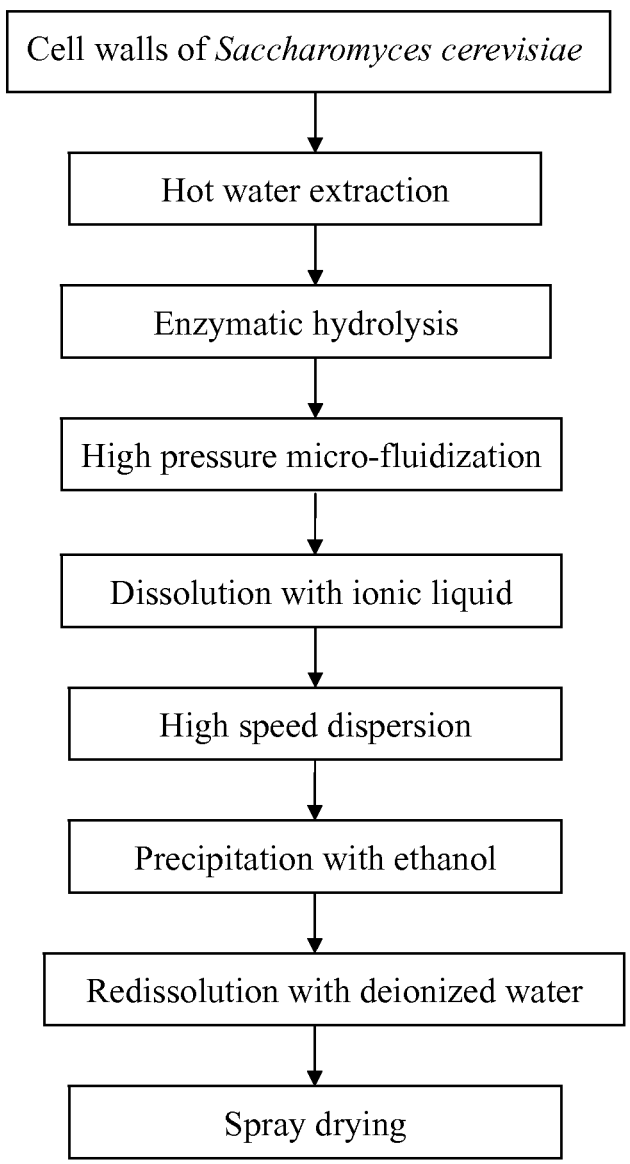

METHOD FOR PREPARING YEAST BETA-D-GLUCAN USING SOLUBILIZATION TECHNOLOGY BASED ON MOLECULAR ASSEMBLY

TECHNICAL FIELD OF THE INVENTION

The present invention belongs to the technical field of food processing, and relates to a method for preparing yeast beta-D-glucan, and in particular to a method for preparing soluble yeast beta-D-glucan of high purity using a solubilization technology based on molecular assembly.

BACKGROUND OF THE INVENTION

Beta-D-glucan is a kind of polysaccharide which widely exists in bacteria, fungi, algae and plants, and one of the main sources of which is *Saccharomyces cerevisiae*. Yeast beta-D-glucan constitutes 30-60% by weight on a dry basis of yeast cell walls, and has a wide variety of physiological functions, such as enhancing immunity, anti-inflammation, antimicrobial, anti-infection, antiviral, anticancer, lowering cholesterol, anti-radiation and healing wounds. China is rich in yeast resources, and the fermentation industry, particularly the brewing industry can produce a large amount of waste *Saccharomyces cerevisiae* each year. In 2013, the beer yield is 50.615 million tons in total, with around 1 million tons of *Saccharomyces cerevisiae* being produced, but most of them are sold only as cheap feeds, or directly discharged into sewers as waste materials. This not only wastes resources, but also causes serious environment pollution. Thus, there is an urgent need for using the modern science and technology to enhance the comprehensive utilization of the waste *Saccharomyces cerevisiae* resources.

Methods for preparing *S. cerevisiae* beta-D-glucan mainly include acid method, alkaline method, enzyme method, ultrasonic method, and the like. There are a variety of preparation methods, but most of them are still limited in industrial scale production. Currently, the method widely used in the industrialized production of *S. cerevisiae* beta-glucan in China is alkaline method, by which the resulting product has high purity. However, the alkaline method would damage the structure of beta-D-glucan, and thus reduce its biological activity and restrict its use. Meanwhile, the alkaline solution would pollute the environment and damage the human health. The interactions of multi-hydroxyl groups in yeast beta-D-glucan molecules will form a compact triple helical structure, and thus making them insoluble in water, which restrict the application of yeast beta-D-glucan in the fields of food, medicine, cosmetics, etc. Therefore, it is very necessary to develop a green technology which is suitable for industrialization to prepare beta-D-glucan with high purity and high solubility under mild conditions.

Dynamic high pressure micro-fluidization (DHPM) technology, as a new means of food processing and handling, is integrated by many unit operations, such as transportation, mixing, superfine grinding, pressurization, heating, puffing, etc. Its working principle is achieving the modification of materials by high speed collision, high frequency oscillation, instantaneous pressure drop, cavitation effect, strong shearing action, etc. DHPM has gradually been widely used in preparation and modification process of polysaccharides.

There are many kinds of designable ionic liquids with unique properties, which can be applied in many fields. Ionic liquids mainly refer to the salts composed of organic cations and inorganic or organic anions, which are in liquid form at or near room temperature. As compared to the traditional organic solvents, ionic liquids have advantages of heat stability, extremely strong solubility, recyclability, and the like. As "green and designable" solvents, ionic liquids have drawn more and more attention in the fields of separation, dissolution, molecular assembly, and the like.

The Chinese patent application for invention with application number 201310003610.2 has disclosed a method for preparing yeast beta-D-glucan. However, the glucan produced by this method has very low solubility so as to be almost insoluble, which greatly limits its biological activity and also limits its practical application in industry.

SUMMARY OF THE INVENTION

In order to solve the problems existed in the prior art, the object of the present invention is to provide a method for preparing soluble yeast beta-D-glucan with high purity using yeast as the raw material. According to the present invention, the green preparation method of yeast beta-D-glucan and the solubilization thereof based on molecular assembly are performed by combining enzymatic treatment, ionic liquid, high pressure micro-fluidization technology so as to obtain yeast beta-D-glucan with higher purity and better solubility.

The technical solution used for achieving the object of the present invention described above is as follows:

A method for preparing yeast beta-D-glucan using a solubilization technology based on molecular assembly, comprising the following steps:

(1) micro-fluidizing an enzymatic hydrolysate of yeast cell walls at 70 to 200 MPa, and then centrifuging to obtain a precipitate;

(2) resuspending the precipitate obtained in step (1) with a ionic liquid, then dispersing to obtain a solution; wherein the ionic liquid is 1-ethyl-3-methylimidazolium acetate or 1-allyl-3-methylimidazolium chloride;

(3) centrifuging the solution obtained in step (2), and then adding ethanol, centrifuging and collecting a precipitate;

(4) resuspending the precipitate obtained in step (3) with water, and then centrifuging and collecting a supernatant.

Preferably, the method further comprises (5): spray drying the supernatant obtained in step (4) to obtain a yeast beta-D-glucan powder.

In step (1) of the method, the enzymatic hydrolysate of yeast cell walls is prepared by the method comprising the following steps:

a. mixing yeast cell walls with water, preferably deionized water, to obtain a suspension, and then centrifuging and collecting a precipitate;

b. resuspending the precipitate obtained in step a with water, preferably deionized water, extracting by heating, and then centrifuging and collecting a precipitate;

c. resuspending the precipitate obtained in step b with water, preferably deionized water, adding snailase or neutral protease to enzymatically hydrolyze so as to obtain an enzymatic hydrolysate.

In step a of the method, preferably, the mass ratio of the yeast cell walls to water is 1:5 to 7; preferably, the centrifuge is performed at a rotating speed of 4000 to 5000 rpm for 5 to 10 min;

In step b of the method, preferably, extracting by heating is performed at the temperature of 80° C. to 95° C.; preferably, the mass ratio of the precipitate to water is 15% to 25%; preferably, the centrifuging is performed at a rotating speed of 4000 to 5000 rpm for 5 to 10 min;

In step c of the method, preferably, the mass ratio of the precipitate to water is 1:3 to 20; preferably the mass of the added enzyme for enzymatic hydrolysis is 0.01% to 0.05% by mass of the precipitate, the temperature of enzymatic hydrolysis is 30° C. to 45° C., and the time for enzymatic hydrolysis is 0.5 to 1.0 hour.

In step (1) of the method, preferably, the micro-fluidization is repeated for 3 to 10 times;

In step (2) of the method, preferably, the precipitate obtained in step (1) is resuspended with the ionic liquid and stirred thoroughly, and then dispersed to obtain a solution; preferably, in the solution, the ratio of the precipitate to the ionic liquid in g: ml is 0.5% to 2.0%; preferably, the dispersing is performed at a rotating speed of 8000 to 10000 rpm for 5 to 8 min;

In step (3) of the method, preferably, the volume of ethanol is 2 to 4 times of the volume of the solution; preferably, the step (3) further comprising washing the precipitate with ethanol for 2 to 3 times to remove the ionic liquid remaining in the precipitate;

In step (4) of the method, preferably, the precipitate obtained in step (3) is resuspended with water and stirred thoroughly, and then centrifuged for collecting a supernatant; preferably, the ratio of the precipitate to water in g:ml is 1:200 to 500; preferably, the centrifuging is performed at a rotating speed of 4500 rpm for 20 min.

In one embodiment according to the present invention, the method of preparing yeast cell walls comprises the following steps: washing the cell walls of *Saccharomyces cerevisiae* as raw materials with water and then centrifuging to remove the impurities, adding water to prepare a suspension, adding NaCl, placing in a constant temperature water bath oscillator under the conditions of pH 5.0 and 55° C. and autolyzing by induction for 24 h, heating to 85° C. and keeping the temperature for 15 min to inactivate the enzyme, centrifuging, and washing the precipitate with water for 3 times.

The present invention also provides yeast beta-D-glucan prepared by the method described above.

The present invention produces the following beneficial effects:

1. The preparation conditions are mild, without the reagents such as strong acids and strong bases which are harmful to the environment, clean and efficient, environment-friendly and safe; the solvent used is ionic liquid, which is green, recyclable, safe and pollution-free.

2. All the instruments used have the corresponding equipments suitable for industrialization, which can realize the industrialization scale production.

3. The present invention can realize comprehensive utilization of waste *Saccharomyces cerevisiae*, a kind of industrial by-product, increase the availability and added value of this industrial by-product, and thus have great economic benefits and environment protection significance.

4. The ionic liquid used can be recovered for recycling, which can reduce the cost, and does not contaminate samples; the resulting yeast beta-D-glucan has high purity and good solubility, which advantageously enlarges its application range.

BRIEF DESCRIPTION OF THE DRAWINGS

FIG. 1 is a flowchart of a method of preparing yeast beta-D-glucan using the solubilization technology based on molecular assembly according to the present invention.

DETAILED DESCRIPTION OF THE INVENTION

FIG. 1 is a flowchart of a method of preparing yeast beta-D-glucan using molecular assembly solubilization technology of the present invention. The present invention is now further illustrated in connection with the examples. It should be understood that the examples are merely used for further illustrating and explaining the present invention and are not used for limiting the present invention.

Unless otherwise stated, all the experimental methods used in the following examples are the conventional methods.

Unless otherwise stated, all the materials, reagents, and the like used in the following examples are commercially available.

The ionic liquids used in the following examples are purchased from Lanzhou Institute of Chemical Physics, Chinese Academy of Science.

The cell walls of *Saccharomyces cerevisiae* used in the following examples are purchased from Senyo Biotechnology Co., Ltd, Zhejiang.

It should be understood that the cell walls of *S. cerevisiae* of the present invention can also be prepared by the following method: washing the cell walls of *S. cerevisiae* as raw materials with water and then centrifuging to remove the impurities, adding water to prepare a suspension, adding NaCl, placing in a constant temperature water bath oscillator under the conditions of pH 5.0 and 55° C. and autolyzing by induction for 24 h, warming to 85° C., keeping the temperature for 15 min to inactivate the enzyme, centrifuging and washing the precipitate with water for 3 times.

Example 1

(1) Adding deionized water to the cell walls of *S. cerevisiae*, stirring to obtain a suspension, centrifuging and washing until the supernatant is clear, and collecting a precipitate;

(2) adding deionized water to the precipitate obtained in step (1) to prepare a solution with a concentration of 15% (w/v) in g/mL, extracting in a constant temperature water bath oscillator under the condition of 95° C. for 4 h, centrifuging at 4500 rpm for 10 min and collecting the precipitate, washing the precipitate with water for 2 times, centrifuging at 4500 rpm for 10 min again and collecting the precipitate;

(3) adding deionized water to the precipitate obtained in step (2) to prepare a solution with a concentration of 20% (w/v) in g/mL, to which is added snailase to enzymatically hydrolyze, and the enzymatically hydrolyzing conditions are as follows: the temperature is 40° C., the adding amount of the enzyme is 0.01%, and the time for hydrolyzing is 3 h; and then treating at 80° C. for 10 min to inactivate the enzyme, and obtaining an enzymatic hydrolysate;

(4) micro-fluidizing and homogenizing the enzymatic hydrolysate at 200 MPa for three times, centrifuging at 4500 rpm for 10 min to obtain a precipitate;

(5) adding ionic liquid, 1-ethyl-3-methylimidazolium acetate to the precipitate obtained in step (4) to prepare a solution with a concentration of 0.5% (w/v) in g/mL, stirring thoroughly to break the strong hydrogen bonding between the triple helical structures of glucans, so that the glucan molecules rearrange and self-assembly to obtain a mixed solution of glucan-ionic liquid;

(6) dispersing the mixed solution obtained in step (5) at high speed of 8000 rpm for 8 min;

(7) adding three times volume of ethanol to the solution obtained in step (6) to precipitate, centrifuging at 4500 rpm for 10 min and collecting the precipitate; washing the precipitate with ethanol repeatedly to remove the ionic liquid remaining in the precipitate, and drying at 70° C. to remove ethanol;

(8) adding deionized water to the precipitate obtained in step (7) to prepare a solution with a concentration of 1% (w/v) in g/mL, stirring thoroughly, and then centrifuging at 4500 rpm for 20 min to obtain a supernatant;

(9) spray drying the supernatant obtained in step (8) to obtain the final yeast beta-D-glucan sample.

The yeast beta-D-glucan obtained in this example is white and fluffy powdered solid, with the yield being 8.2% (based on the raw materials), the purity being 93.6%, and the solubility being 88.6%.

Example 2

Adding deionized water to the cell walls of S. cerevisiae, stirring to obtain a suspension, centrifuging and washing until the supernatant is clear, and collecting a precipitate;

adding deionized water to the precipitate obtained in step (1) to prepare a solution with a concentration of 25% (w/v) in g/mL, extracting in a constant temperature water bath oscillator under the condition of 95° C. for 4 h, centrifuging at 5000 rpm for 5 min and collecting the precipitate, washing the precipitate with water for 2 times, centrifuging at 5000 rpm for 5 min again and collecting the precipitate;

adding deionized water to the precipitate obtained in step (2) to prepare a solution with a concentration of 15% (w/v) in g/mL, to which is added neutral protease to enzymatically hydrolyze, and the enzymatically hydrolyzing conditions are: the temperature is 45° C., the adding amount of the enzyme is 0.05%, and the time for hydrolyzing is 1 h; and then treating at 80° C. for 10 min to inactivate the enzyme, and obtaining an enzymatic hydrolysate;

micro-fluidizing and homogenizing the enzymatic hydrolysate at 150 MPa for five times, centrifuging at 5000 rpm for 5 min to obtain a precipitate;

adding ionic liquid, 1-allyl-3-methylimidazolium chloride to the precipitate obtained in step (4) to prepare a solution with a concentration of 2.0% (w/v) in g/mL, stirring thoroughly to break the strong hydrogen bonding between the triple helical structures of glucans, so that the glucan molecules rearrange and self-assembly to obtain a mixed solution of glucan-ionic liquid;

dispersing the mixed solution obtained in step (5) at high speed of 10000 rpm for 5 min;

adding three times volume of ethanol to the solution obtained in step (6) to precipitate, centrifuging at 5000 rpm for 5 min and collecting the precipitate; washing the precipitate with ethanol repeatedly to remove the ionic liquid remaining in the precipitate, and drying at 70° C. to remove ethanol;

adding deionized water to the precipitate obtained in step (7) to prepare a solution with a concentration of 0.5% (w/v) in g/mL, stirring thoroughly, and then centrifuging at 4500 rpm for 20 min to obtain a supernatant;

spray drying the supernatant obtained in step (8) to obtain the final yeast beta-D-glucan sample. The yeast beta-D-glucan obtained in this example is white and fluffy powdered solid, with the yield being 8.7% (based on the raw materials), the purity being 92.7%, and the solubility being 87.6%.

While the present invention has been described in some extent, it is obviously that modification of various conditions can be made properly without departing the spirit and scope of the present invention. It can be understood that the present invention does not limit to the embodiments described, but belongs to the scope of the claims which include the equivalents to each element.

What is claimed is:

1. A method for preparing yeast beta-D-glucan using a solubilization technology based on molecular assembly, characterized in that the method consists of the following steps:
   (I) mixing yeast cell walls with water to obtain a suspension, and then centrifuging and collecting a centrifugate;
   (II) resuspending the centrifugate obtained in step (I) with water, extracting by heat, and then centrifuging and collecting the centrifugate;
   (III) resuspending the centrifugate obtained in step (II) with water, adding a mixed enzyme comprising an endoglucanase, exoglucanase, and β-glucosidase or a neutral protease to enzymatically hydrolyze so as to obtain an enzymatic hydrolysate;
   (IV) micro-fluidizing the enzymatic hydrolysate of yeast cell walls prepared in step (III) at 70 to 200 MPa, and then centrifuging to obtain a centrifugate;
   (V) resuspending the centrifugate obtained in step (IV) with an ionic liquid, then dispersing to obtain a solution; wherein the ionic liquid is 1-ethyl-3-methylimidazolium acetate or 1-allyl-3-methylimidazolium chloride;
   (VI) centrifuging the solution obtained in step (V), and then adding ethanol, and collecting a centrifugate after recentrifuging; and
   (VII) resuspending the centrifugate obtained after recentrifuging in step (VI) with water, and then centrifuging and collecting a supernatant.

2. The method according to claim 1, characterized in that in step (I) of the method, the mass ratio of the yeast cells to water is 1:5 to 7.

3. The method according to claim 1, characterized in that in step (II) of the method, extracting by heat is performed at the temperature of 80° C. to 95° C.

4. The method according to claim 1, characterized in that in step (III) of the method, the mass ratio of the centrifugate to water is 1:3 to 20.

5. The method according to claim 1, characterized in that in step (V) of the preparation method, the centrifugate obtained in step (IV) is resuspended with the ionic liquid and stirred thoroughly, and then dispersed to obtain a solution.

6. The method according to claim 1, characterized in that in step (VI) of the preparation method, the volume of ethanol is 2 to 4 times of the volume of the solution.

7. The method according to claim 1, characterized in that in step (VII) of the preparation method, the centrifugate obtained in step (VI) is resuspended with water and stirred thoroughly, and then centrifuged for collecting a supernatant.

8. The method according to claim 1, characterized in that in the method for preparing the enzymatic hydrolysate of the yeast cell walls, the water is deionized water.

9. The method according to claim 1, characterized in that in step I of the method, the centrifuge is performed at a rotating speed of 4000 to 5000 rpm for 5 to 10 min.

10. The method according to claim 1, characterized in that in step II of the method, the mass percentage of the centrifugate to water is 15% to 25%.

11. The method according to claim 1, characterized in that in step II of the method, the centrifuging is performed at a rotating speed of 4000 to 5000 rpm for 5 to 10 min.

12. The method according to claim 1, characterized in that in step III of the method, the added mass of the enzyme for enzymatic hydrolysis is 0.01% to 0.05% by mass of the centrifugate, the temperature of enzymatic hydrolysis is 30° C. to 45° C., and the time for enzymatic hydrolysis is 0.5 to 1.0 hour.

13. The method according to claim 1, characterized in that in step (V) of the preparation method, in the solution, the percentage of the centrifugate to the ionic liquid in g per ml is 0.5% to 2.0%.

14. The method according to claim 1, characterized in that in step (V) of the preparation method, the dispersing is performed at a rotating speed of 8000 to 10000 rpm for 5 to 8 min.

15. The method according to claim 1, characterized in that in step (VII) of the preparation method, the ratio of the centrifugate to water in g per ml is 1:200 to 500.

16. The method according to claim 1, characterized in that in step (VII) of the preparation method, the centrifuging is performed at a rotating speed of 4500 rpm for 20 min.

17. A method for preparing yeast beta-D-glucan using a solubilization technology based on molecular assembly, characterized in that the method consists of the following steps:
(I) washing the cell walls of *Saccharomyces cerevisiae* as raw materials with water and then centrifuging to remove the impurities, adding water to prepare a suspension, adding NaCl, placing in a constant temperature water bath oscillator under the conditions of pH 5.0 and 55° C. and autolyzing by induction for 24 h, heating to 85° C., keeping the temperature for 15 min to inactivate an enzyme, centrifuging, and washing the centrifugate with water for 3 times;
(II) mixing yeast cell walls with water to obtain a suspension, and then centrifuging and collecting a centrifugate;
(III) resuspending the centrifugate obtained in step (II) with water, extracting by heat, and then centrifuging and collecting the centrifugate;
(IV) resuspending the centrifugate obtained in step (III) with water, adding a mixed enzyme comprising an endoglucanase, exoglucanase, and β-glucosidase or a neutral protease to enzymatically hydrolyze so as to obtain an enzymatic hydrolysate;
(V) micro-fluidizing the enzymatic hydrolysate of yeast cell walls prepared in step (IV) at 70 to 200 MPa, and then centrifuging to obtain a centrifugate;
(VI) resuspending the centrifugate obtained in step (V) with an ionic liquid, then dispersing to obtain a solution; wherein the ionic liquid is 1-ethyl-3-methylimidazolium acetate or 1-allyl-3-methylimidazolium chloride;
(VII) centrifuging the solution obtained in step (VI), and then adding ethanol, and collecting a centrifugate after recentrifuging; and
(VIII) resuspending the centrifugate obtained after recentrifuging in step (VII) with water, and then centrifuging and collecting a supernatant.

18. A method for preparing yeast beta-D-glucan using a solubilization technology based on molecular assembly, characterized in that the method consists of the following steps:
(I) mixing yeast cell walls with water to obtain a suspension, and then centrifuging and collecting a centrifugate;
(II) resuspending the centrifugate obtained in step (I) with water, extracting by heat, and then centrifuging and collecting the centrifugate;
(III) resuspending the centrifugate obtained in step (II) with water, adding a mixed enzyme comprising an endoglucanase, exoglucanase, and β-glucosidase or a neutral protease to enzymatically hydrolyze so as to obtain an enzymatic hydrolysate;
(IV) micro-fluidizing the enzymatic hydrolysate of yeast cell walls prepared in step (III) at 70 to 200 MPa, and then centrifuging to obtain a centrifugate;
(V) resuspending the centrifugate obtained in step (IV) with an ionic liquid, then dispersing to obtain a solution; wherein the ionic liquid is 1-ethyl-3-methylimidazolium acetate or 1-allyl-3-methylimidazolium chloride;
(VI) centrifuging the solution obtained in step (V), and then adding ethanol, and collecting a centrifugate after recentrifuging;
(VII) resuspending the centrifugate obtained after recentrifuging in step (VI) with water, and then centrifuging and collecting a supernatant; and
(VIII) spray drying the supernatant obtained in step (VII) to obtain a yeast beta-D-glucan powder.

19. A method for preparing yeast beta-D-glucan using a solubilization technology based on molecular assembly, characterized in that the method consists of the following steps:
(I) mixing yeast cell walls with water to obtain a suspension, and then centrifuging and collecting a centrifugate;
(II) resuspending the centrifugate obtained in step (I) with water, extracting by heat, and then centrifuging and collecting the centrifugate;
(III) resuspending the centrifugate obtained in step (II) with water, adding a mixed enzyme comprising an endoglucanase, exoglucanase, and β-glucosidase or a neutral protease to enzymatically hydrolyze so as to obtain an enzymatic hydrolysate;
(IV) micro-fluidizing the enzymatic hydrolysate of yeast cell walls prepared in step (III) at 70 to 200 MPa, and then centrifuging to obtain a centrifugate;
(V) resuspending the centrifugate obtained in step (IV) with an ionic liquid, then dispersing to obtain a solution; wherein the ionic liquid is 1-ethyl-3-methylimidazolium acetate or 1-allyl-3-methylimidazolium chloride;
(VI) centrifuging the solution obtained in step (V), and then adding ethanol, and collecting a centrifugate after recentrifuging; washing the centrifugate after recentrifuging with ethanol for 2 to 3 times to remove the ionic liquid remaining in the centrifugate; and
(VII) resuspending the centrifugate obtained after washing in step (VI) with water, and then centrifuging and collecting a supernatant.

* * * * *